United States Patent [19]

Crawford, Jr.

[11] 4,158,196

[45] Jun. 12, 1979

[54] MAN-MACHINE INTERFACE SYSTEM

[76] Inventor: George E. Crawford, Jr., 66 Dean St., Franklin, Mass. 02038

[21] Appl. No.: 786,232

[22] Filed: Apr. 11, 1977

[51] Int. Cl.$^2$ .................... H04Q 9/00; A61B 5/00; B62D 1/00

[52] U.S. Cl. .................................. 340/163; 3/1.1; 180/6.5; 318/580; 340/147 R; 244/83 D

[58] Field of Search ............... 340/163, 147 R, 365 P, 340/150; 318/580, 587; 180/6.5; 244/83 D, 83 E; 128/2.1 B, 2.1 R, 419 P, 2.06, 2.1 M; 3/1.1

[56] References Cited

U.S. PATENT DOCUMENTS

| | | | |
|---|---|---|---|
| 3,106,371 | 10/1963 | Brannin et al. | 318/580 X |
| 3,374,845 | 3/1968 | Selwyn | 180/6.5 |
| 3,623,477 | 11/1971 | Trent | 128/2.1 B |
| 3,780,724 | 12/1973 | John | 128/2.1 R |
| 3,893,450 | 7/1975 | Ertl | 128/2.1 B |
| 3,920,024 | 11/1975 | Bowers | 128/419 P |
| 3,942,516 | 3/1976 | Glynn et al. | 128/2.1 B |
| 3,983,865 | 10/1976 | Shepard | 128/2.1 M |
| 3,986,030 | 10/1976 | Teltscher | 340/365 P |
| 4,030,141 | 6/1977 | Graupe | 3/1.1 |
| 4,047,159 | 9/1977 | Boudry | 340/150 |

Primary Examiner—Donald J. Yusko
Attorney, Agent, or Firm—Wolf, Greenfield & Sacks

[57] ABSTRACT

The system provides a direct electrical interface between the electrical activity that may be self-induced in the human nervous system and the electrical activity in devices such as computers or calculators. Either one-way or two-way communication and/or control may be provided. For man-to-machine (efferent) communication bioelectric activity is monitored with electrodes and the action potentials which are self-generated are converted into digital signals preferably in the form of binary signals which may be interpreted by digital computers, micro-processors or other logic systems. For machine-to-man (afferent) communication binary signals in the form of binary ones or zeros are converted to action potentials. Depending upon the particular application, different codes are used to give specific meanings to specific patterns of bioelectric activity that the operator generates and specific patterns of electric stimulation that the operator receives. For example, if the system is used to replace a teletype terminal used to communicate with the computer, each specific pattern generated by the operator corresponds to a keyboard character with the need in this case for multiple channels for communication. In one system according to the invention the control is used by a handicapped person to manipulate a wheelchair with each specific pattern of bioelectric activity corresponding to a direction of movement of the wheelchair. In the wheelchair application two-way communication is provided and binary signals are generated from two separately excitable electrode sites with the code being sent employing successive communication time slots. For any given application, the operator is required to learn an appropriate code. After sufficient practice, the codes become subliminal in the same way as an experienced typist is not consciously concerned with the details of the finger movement.

19 Claims, 7 Drawing Figures

| MOTOR SWITCHING FUNCTION | COMMAND | | | |
|---|---|---|---|---|
| | FORWARD | RIGHT | LEFT | REVERSE |
| RIGHT WHEEL FORWARD | X | | X | |
| RIGHT WHEEL REVERSE | | | | X |
| LEFT WHEEL FORWARD | X | X | | |
| LEFT WHEEL REVERSE | | | | X |

Fig 4

| EMG CHANNEL | T1 | T2 | COMMAND |
|---|---|---|---|
| RIGHT | X | | FORWARD |
| LEFT | | X | |
| RIGHT | X | X | RIGHT |
| LEFT | | | |
| RIGHT | | | LEFT |
| LEFT | X | X | |
| RIGHT | | X | REVERSE |
| LEFT | X | | |
| RIGHT | X | | STOP |
| LEFT | X | | |

MAN-MACHINE INTERFACE SYSTEM

BACKGROUND OF THE INVENTION

The present invention relates in general to a direct, electrical, man-machine interface system. More particularly, the present invention is concerned with a man-machine interface system that permits direct communication with a digital device such as a computer, microprocessor or calculator. The system of this invention may also be implemented as a two-way communication system permitting the conversion of bioelectric activity into digital signals and vice-versa.

Man is becoming continuously more dependent upon the services of computers, micro-processors, hard-wired logic circuitry and mechanical and electrical devices that are controlled and/or monitored by these digital devices. Of course, in order for electrically controlled machinery to serve man, provisions must be made for man-machine interfaces. Typical devices presently used for performing this interface function are teletype terminals and similar keyboards, cathode ray tube displays, consoles with switches and indicator lamps, card readers, and magnetic tape drives.

A limited number of special purpose systems have been developed to control prosthetic devices such as artificial limbs by using amplified and rectified myoelectric signals to switch on drive motors. However, these systems are not capable of direct electrical interface with a digital system such as a computer or calculator. These systems do not provide coding for controlling a digital system but simply convert directly a self-induced bioelectric activity into a mechanical action.

Accordingly, one object of the present invention is to provide a direct electrical man-machine interface system for permitting direct communication between the human nervous system and a man-made digital system. In accordance with the object of this invention there is no longer the need for awkward interface devices such as keyboards, switches and displays.

Another object of the present invention is to provide a man-machine interface system for converting bioelectrical activity to either a single channel or multi-channel stream of digital signals that can serve as an input to a computer, micro-processor, discreet logic network or any system using digital input signals. These digital input signals are usually in binary form in binary ones and zeros.

A further object of the present invention is to provide a man-machine interface system that additionally provides information flow from the digital system to the operator by converting digital signals into electrical stimuli induced in the operator.

Still another object of the present invention is to provide an interface system that provides different time slots for code communication, preferably in combination with acknowledgement signals transferred from the digital system to the operator.

SUMMARY OF THE INVENTION

To accomplish the foregoing and other objects of this invention there is provided, apparatus for direct electrical man-machine communication comprising electrode means for detecting bioelectric signals which are then preferably electronically amplified and converted to a digital format preferably using digital signal processing circuitry. The electrode means may comprise surface electrodes, implanted electrodes or any other type that may be used to monitor bioelectric activity in muscle fibers, nerve cells, or nerve fibers. The amplifier that is used for amplifying the bioelectric signals provides adequate gain for these signals suitable for triggering standard digital logic. The amplifier also provides pass band filtering to eliminate noise at frequencies that contain little energy of the bioelectric signal spectrum and has an adequate low noise figure to prevent masking the weak bioelectric signals with amplifier noise. In addition, for multichannel, two-way communication systems, the amplifier inputs are isolated from each other and from any common ground to prevent the conduction of stimulating current from a desired stimulation site to other sites, resulting in cross talk among the channels. The digital signal processing circuitry may comprise a threshhold detector, the output of which triggers a monostable multi-vibrator which in turn generates a standard digital pulse preferably of predetermined width.

For machine-to-man information transfer, digital pulses are converted into bioelectric stimulation pulses that are applied to the operator with electrodes. With the use of an appropriate multiplexer the same electrodes may be used as were used for information flow from the operator (efferent flow direction). In one form a digital pulse is used to trigger a monostable multi-vibrator that has an "on" time equal to the desired width of the stimulation pulse. The output of the multi-vibrator is used to gate a constant current source. The use of a constant current source is convenient to maintain the stimulation level in the limited dynamic range between the threshhold of detection and the threshhold of an unpleasant shocking effect, as the electrode impedance varies over a period of time. For multi-channel operation, output isolation using such techniques as optical coupling or transformer coupling is used to confine the stimulation for each channel to the desired location.

In accordance with the invention information transfer can occur either in serial fashion or in parallel fashion. For parallel transfer a number of channels are used and an entire binary word is communicated in parallel. For serial communication in a simplified system disclosed herein two channels are used and the signals are communicated in successive time slots. These time slots may be separated by an acknowledgement time period wherein a signal is coupled from the digital system to the operator indicating receipt in the first code in the first time slot. In another system using a simple code there are provided two channels, one for representing a dot and the other for representing a dash thereby allowing the use of Morse code that the user may already be familiar with.

BRIEF DESCRIPTION OF THE DRAWINGS

Numerous other objects, features and advantages of the invention should now become apparent upon a reading of the following detailed description taken in conjunction with the accompanying drawings, in which.

DETAILED DESCRIPTION

Figure 1:
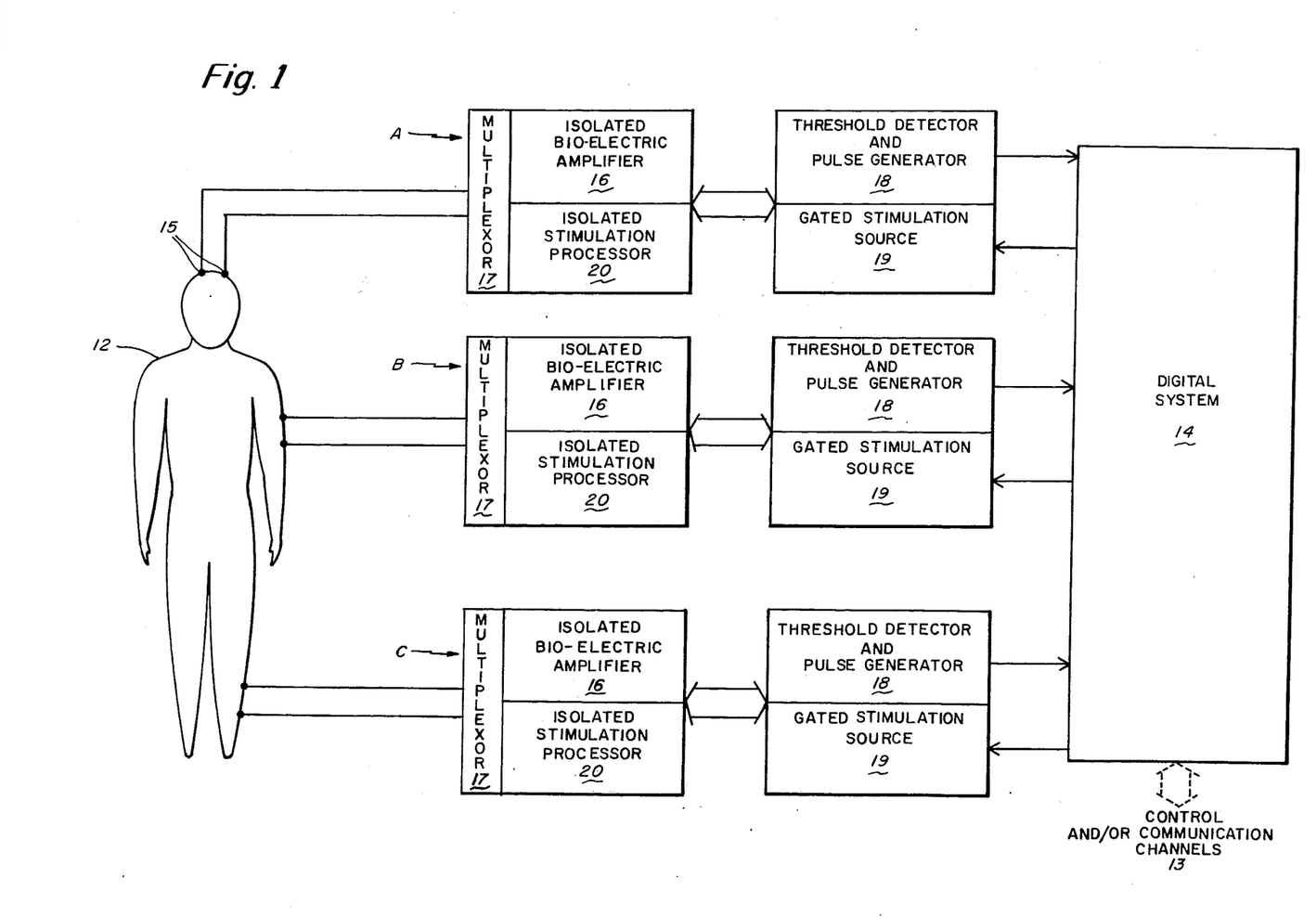
FIG. 1 is a general block diagram of a direct-electrical, two-way, multi-channel, man-machine interface system constructed in accordance with the principles of this invention.

Referring to FIG. 1 there is shown a block diagram of one embodiment of the present invention employing a plurality of communication channels interfacing between a human operator and a digital system which may be a computer or micro-processor. FIG. 1 shows channels A, B and C coupling between the human operator 12 and the digital system 14. The digital system 14 as noted, is provided with control and/or communication channels 13 over which the operator 12 may transmit information and from which he may receive information. The digital system 14 may comprise an encoder/decoder that translates between the operator's code and useful inputs and outputs between the operator and the channels 13. For other embodiments of the system of this invention the digital system 14 may be used directly without control and/or communication channels 13. For example, the digital system 14 may comprise an electronic calculator being used by the operator.

In man-to-machine communication, the operator 12 is taught to generate one or more action potentials from one or more specific nerve cells, nerve fibers or muscles in accordance with a predetermined code. For each action potential self-induced by the operator 12 an electric field results and there is thus the development of a small voltage between an appropriately positioned pair of electrodes 15. This voltage is amplified by the isolated bioelectric amplifier 16. The same pair of electrodes is also used as shown in FIG. 1 for information coming to the operator. Multiplexer circuitry 17 is used for rooting the monitored bioelectric signal to the input of amplifier 16. The miniature amplifier 16 is mounted directly at the electrode site and results in the elimination of interfering signal pick-up that would occur if the low level bioelectric signal were passed any significant distance over wires prior to amplification. Differential amplification can be used for interference reduction.

For systems using multiple electrode sites and multiple information channels, it is preferred that the output of the amplifier and any power leads to the amplifier be isolated from the following circuitry 18. This isolation may be provided by providing optical coupling or magnetic coupling. The purpose of this is to prevent stimulating current used for transmitting information to the operator from leaking between electrode sites and causing confusion as to which channels was activated. The analog signal from the amplifier 16 is essentially transformed by the signal processing circuitry 18 to a digital voltage level which may be considered a one or zero logic level. One form of signal processing circuitry may comprise a threshhold detector followed by a monostable multi-vibrator and is triggered when the threshhold is exceeded. The "on" time of the monostable multi-vibrator is slightly longer than the duration of a typical bioelectric burst, resulting in one standard output pulse per bioelectric burst. The presence of such a pulse may represent a digital one while the absence of the pulse may represent a digital zero.

For communication from the digital system 14 to the nervous system of the operator there is provided in each of the channels a gated stimulation source 19 and an isolated stimulation processor 20. When a transition occurs in the digital system 14 such as from a one to a zero (or vice-versa) of an output line from the digital system 14 the stimulation source 19 is gated. A typical embodiment of the gated stimulation source may comprise a radio frequency power oscillator that is switched on by the output level of a monostable multi-vibrator. The monostable multi-vibrator is triggered by a transition in the level on the output line from the digital system 14 and has an "on" time equal to the desired duration of the stimulation pulse. If more than one stimulation channel is used with an operator as shown in FIG. 1, electrical isolation is provided between channels to prevent stimulation current applied to one electrode site from returning via the common connection at other sites, a condition that would create confusion, (cross talk) between channels. Two types of cross talk may occur. The first type results from confusion as to at which site the stimulus is felt. The second type results from the electric current traveling the relatively long distances between sites which causes interference with all EMG channels having electrodes in the electric field produced by this current flow. The first type may be eliminated if each pair of stimulating electrodes consisted of a small center electrode and a second electrode encircling it. But the resultant confinement of the highest current density to the small center electrode does not prevent a return flow to other electrode sites. Thus, the isolation is still required to prevent the second type of cross talk.

A typical embodiment of the isolation unit 20 may comprise a transformer with no electrical connection between primary and secondary and a rectifier and DC current regulator. The current regulator may comprise a series pass transistor connected so that the output current is independent of the load impedance presented by the electrodes 15. This would maintain the stimulation current within the narrow dynamic range between the threshhold of detection of the operator and the threshhold of an unpleasant shocking effect. If the same pair of electrodes is used for information coming from the operator, a simple multiplexer circuit 17 may be used to root the stimulating current to the operator.

Figure 2:
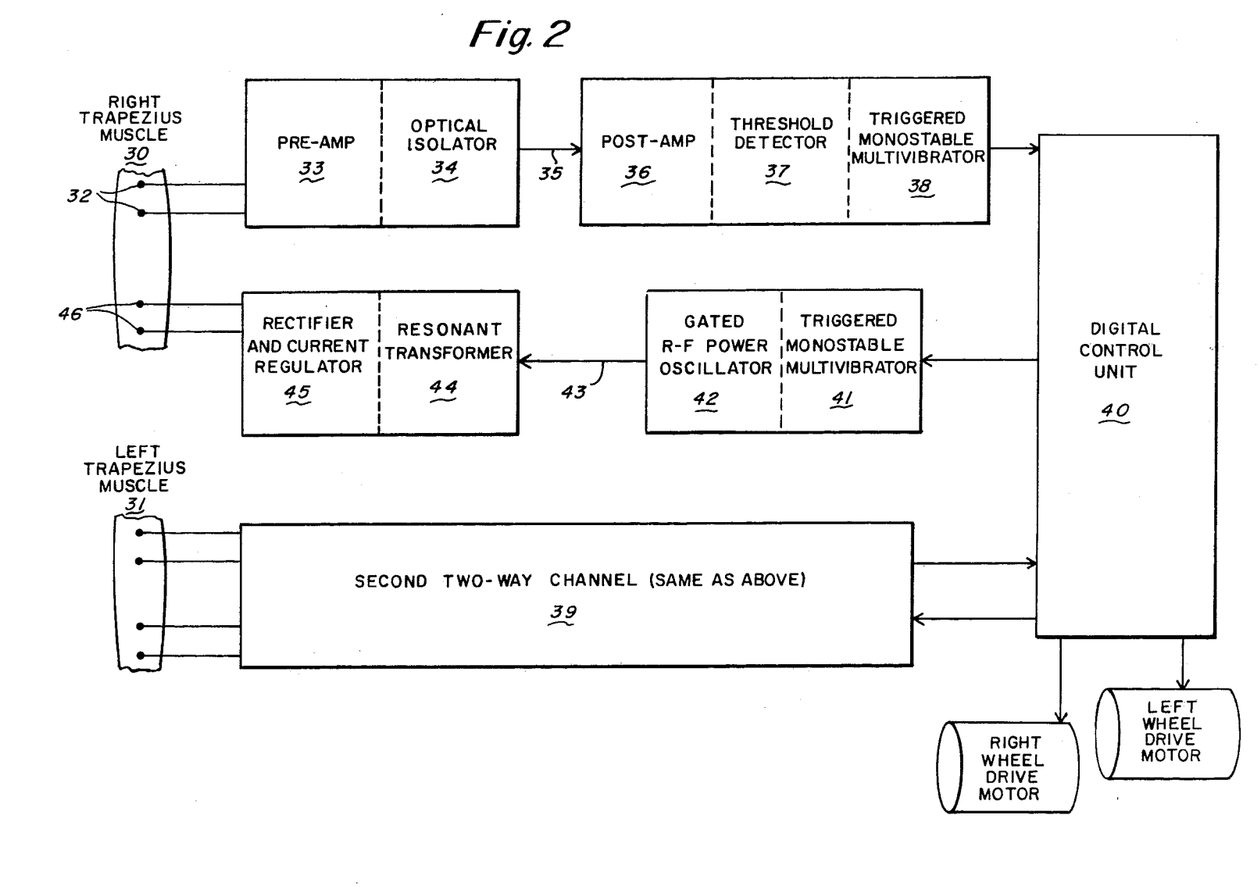
FIG. 2 shows a more specific block diagram of the embodiment of the general system shown in FIG. 1 for the control of a powered wheelchair.

FIG. 2 shows a more specific application than the general system shown in FIG. 1. The embodiment of FIG. 2 is for providing wheelchair control using predetermined coded signals from the operator. This system allows an individual with injury high in the spinal cord resulting in loss of function of both arms and legs (a quadriplegic) to operate a powered wheelchair without the need to resort to the awkward chain bar or puff-and-sip systems that are currently known.

In the embodiment of FIG. 2 the operator of the wheelchair generates commands in the form of coded patterns of action potentials in the fibers of the upper portions of the trapezius muscles including the right trapezius muscle 30 and the left trapezius muscle 31.

The two trapezius muscles extend up the back and into the neck, one on the right side and one on the left side. These muscles were chosen for use in this particular embodiment of the invention because even a person with injury high in the spinal cord area can generate electrical activity in the upper portions of these muscles by attempting to make minute twitches of the muscles.

The electrical activity in the right trapezius muscle 30 produces a voltage between the two monitoring electrodes 32 when the activity has been self-induced by the operator. This bioelectric signal is amplified by the preamplifier 33 and couples to the cable 35 via the optical isolator 34. The preamplifier 33 and the optical isolator 34 may be contained in a relatively small module directly disposed adjacent to the electrodes 32. The signal passes through the optical isolator as an infrared light beam that is generated by a light emitting diode and detected by a photo transistor. This arrangement provides complete electrical isolation between the miniature module consisting of electrodes 32, preamplifier 33, optical isolator 34, and a battery, and the remainder of the apparatus connected after the cable 35. The preamplifier 33 provides adequate gain to insure that the system noise figure is not degraded by the insertion loss of the optical isolator 34 and the noise of the post amplifier 36. The miniature module, which is attached to the operator over the trapezius muscle with stretch bandages, provides an output of adequately high level and low impedance to result in a high ratio of bioelectrical signal to interference picked up by the cable 35. The post amplifier 36 provides additional gain so as to provide an adequate input level for the threshhold detector 37. The threshhold is set at a level above the background noise, but below the level that results from the generation of a bioelectric control signal. The output of the threshhold detector 37 triggers a monostable multivibrator 38. The "on" time of the monostable multivibrator is set to be equal to the longest expected duration of a burst of bioelectric control activity. As a result, each control burst produces one, and only one, output pulse of a standard amplitude and duration from the multi-vibrator 38. Similar pulses may be initiated by electrical activity in the left trapezius muscle 31 with the use of an identical second channel 39.

Figure 3:
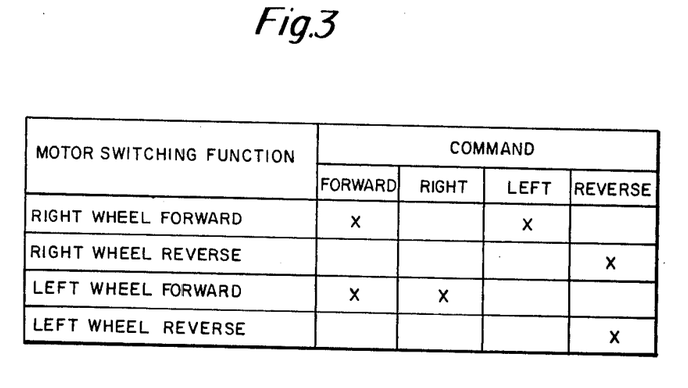
FIG. 3 is a table associated with the diagram of FIG. 2 and showing how each of the wheelchair drive motors are switches for each of the four activating commands shown.

The digital control unit 40 decodes pulses from the two channels to control the wheelchair. Five different commands from the operator can be decoded: FORWARD, initiate motion in the straight ahead direction; RIGHT, initiate motion that is both forward and to the right; LEFT, initiate motion that is both forward and to the left; REVERSE, initiate motion in the straight backward direction; and STOP, stop any motion. The effects of these commands are not additive or accumulative. Each time a command is given, the effect of the previous command is negated. The four activating commands turn on motors as shown in FIG. 3. The STOP command turns off any motor activity resulting from the previous command.

Figure 4:
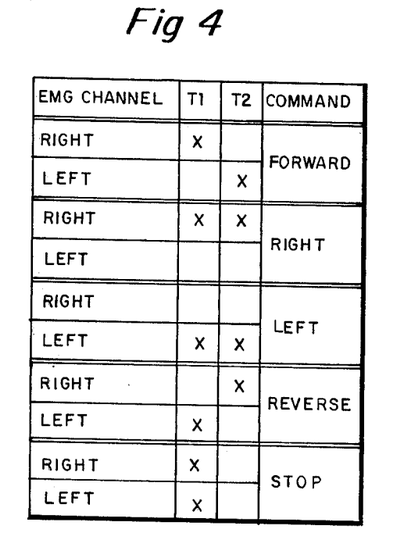
FIG. 4 is a second table associated with the diagram of FIG. 2 which shows how the commands for operating the wheelchair are coded in terms of bioelectric activity in two different muscles during two sequential time intervals.

The code for translating electrical pulses from the two control channels into the five wheelchair commands is summarized in FIG. 4. Two sequential time intervals T1 and T2 are used for each command except the STOP command. The first time interval T1 is initiated by the operator whenever he chooses to make a command. This requires that each of the five commands is coded such that bioelectric activity occurs during the T1 time interval.

Only the STOP command is coded for activity on both channels during the time interval T1. This allows the digital control unit 40 to execute the STOP command without delaying until the time interval T2. This choice of coding has an additional safety feature in that if both channels should become activated due to the operator becoming alarmed or having a muscle spasm, the chair will immediately stop.

After receiving an input from only one of the two channels during the time interval T1, the digital control unit 40 interrogates the patient for the next response which will occur during the time interval T2. This interrogation is made by electrical stimulation via one of the two stimulation channels shown in FIG. 2. The other stimulation channel may be used for a slightly different purpose by providing feedback whenever the operator generates an excessive bioelectric activity. The object of this feedback is to train the operator to use minute muscular twitches rather than gross movements.

The digital control unit 40 delays the interrogation for the T2 interval bioelectric response by the maximum expected differential between the arrival times of the two interval T1 pulses that are intended by the operator to be simultaneous. This delay is required to discriminate between a STOP COMMAND and the first pulse of an activating command. It is expected that this differential interval will be less than 100 milliseconds for most operators. The delay time may be made adjustable so that it can be decreased as the operator becomes more proficient.

Immediately upon receipt of the next signal after the interrogation stimulus which should be a signal from only one of the channels, the appropriate command (FORWARD, RIGHT, LEFT OR REVERSE) is executed. The code of FIG. 4 is purposefully structured so that no command requires activation of both channels during the time interval T2. This avoids the necessity of waiting for a second interval of the maximum differential time between arrival of pulses that are intended to be simultaneous.

For a practiced operator, the delay between the interrogation by electrical stimulation and the interval T2 response is considerably less than the response times that experimental psychologists measure for unexpected stimuli usually in the order of 200 milliseconds. This occurs because of the anticipation of the interrogation. The effective response time to the interrogation however, cannot be reduced to zero because of the human inability to function as a precision clock. Operators learn to avoid overanticipation that result in the generation of an interval T2 response before the electrical stimulus. As can be seen from FIG. 4 if this were done when either a FORWARD or REVERSE command were intended a STOP command results.

A beginning operator is allowed a large differential interval for the two simultaneous pulses required for the STOP command. He is also allowed a long duration for bioelectric bursts. These adjustable parameters may be tightened up as performance improves.

Figure 5:
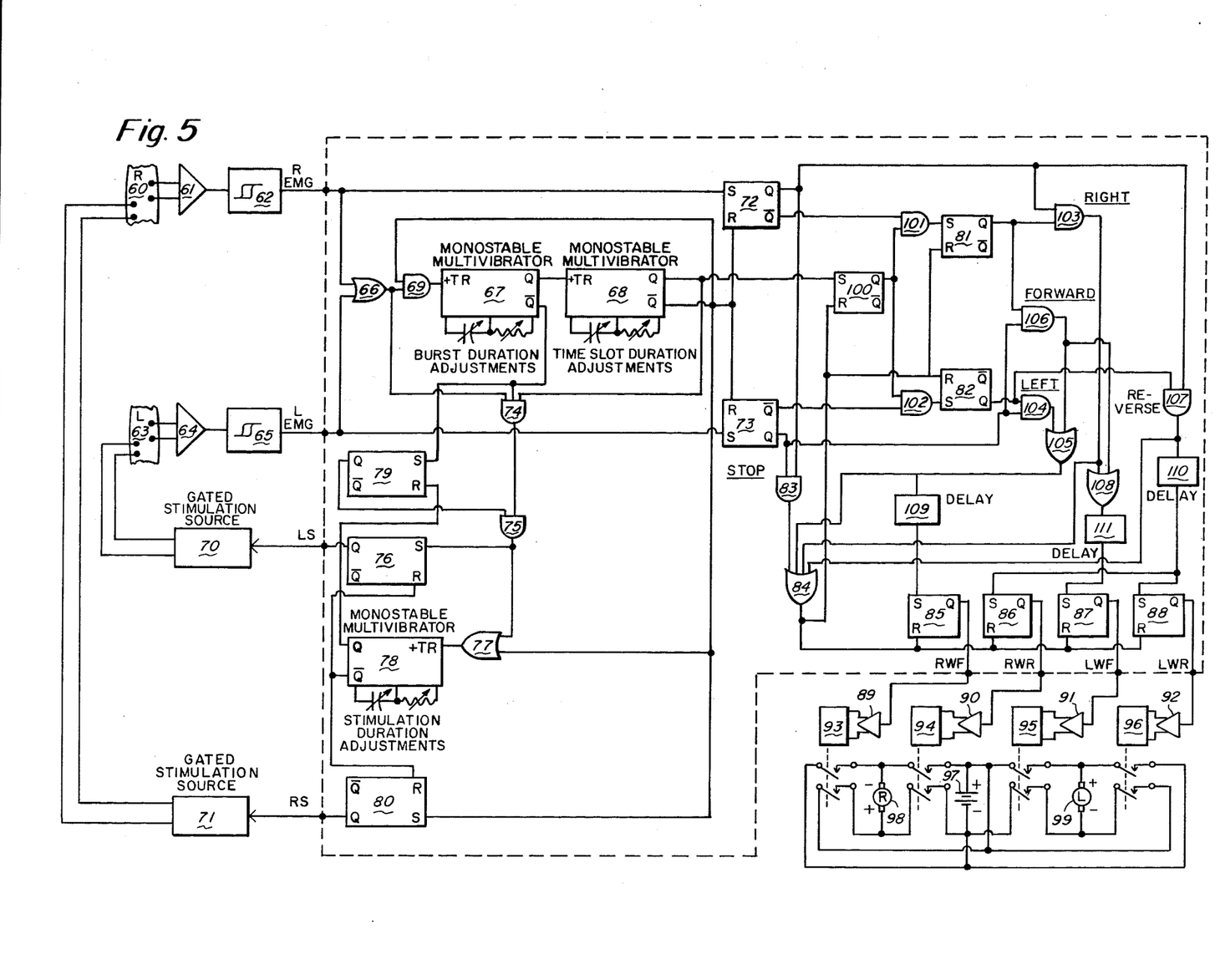
FIG. 5 is a logic diagram for a hard-wired logic system that could be used as the digital control unit shown in FIG. 2.

The digital control unit 40 of FIG. 2 can be implemented with a hard-wired system consisting of the appropriate logic elements such as gates, flip-flops, and monostable multivibrators. Such a system is shown in FIG. 5. Electrodes on the right trapezius muscle 60 provide an input for the isolated amplification system 61. This isolated amplification system 61 corresponds to the preamplifier 33 of FIG. 2, the optical isolator 34 of FIG. 2, and the postamplifier 36 also of FIG. 2. The Schmitt trigger 62 of FIG. 5 implements the function of the threshhold detector 37 of FIG. 2. The corresponding components for the left efferent channel of FIG. 5 are the isolated amplification system 64 and the Schmitt trigger 65.

The system of FIG. 5 differs from that of FIG. 2 in that an R-S (reset-set) flip-flop 72 of FIG. 5 is used in place of the triggered monostable multivibrator 38 of FIG. 2. This R-S flip-flop 72 is triggered by right channel EMG bursts that exceed the threchhold of the Schmitt trigger 62. It is reset by an output from the monostable multivibrator 68 that serves the same timing function as the triggered monostable multivibrator 38 of FIG. 2, but in addition, is common to both the right and left EMG channels. The OR gate 66 is used so that EMG activity on either channel will trigger the common timing monostable multivibrator 68. The R-S flip-flop 73 provides a standard pulse for each left channel EMG burst in the same manner that the R-S flip-flop 72 does for the right channel. The on-time of the monostable multivibrator 68 which determines the durations of these standard pulses is the time slot, T1 or T2 of FIG. 4, for either of the two sequential components of the commands tabulated in FIG. 4. This time is made adjustable so that it can be decreased as an operator's proficiency increases. The use of a common monostable multivibrator for both channels avoids the necessity of making an adjustment for each channel which would require either a ganged control or the adjustment of two controls.

EMG activity on either the right or left channel triggers a monostable multivibrator 67 that times for the maximum allowable burst duration in addition to triggering the time slot multivibrator 68. This burst duration multivibrator 67 is used to implement the training feature by which feedback is provided to the operator when he uses excessive muscular activity to generate the EMG's. The on-time of this multivibrator 67 is set to the duration of an EMG burst that would result from the use of excessive muscular activity. This time duration can be reduced as the operator gains proficiency at generating very minute muscular twitches. This allowable burst duration time must be set such that it is less than a time slot duration in order for the feedback mechanism, described below, which informs the operator of excessive burst duration, to function.

The retriggering of the burst duration multivibrator 67 during the period that begins when it returns to its stable state and ends when the slot duration multivibrator 67 returns to its stable state could cause a malfunction. This malfunction would result from the burst duration monostable multivibrator 67 being on when the system should be ready to initiate the next time slot. To prevent a long EMG burst from causing such an undesired retriggering, the monostable multivibrator triggering mechanism is made inactive for the total time slot duration by ANDing the trigger input with the inverting output of the slot duration monostable multivibrator. This ANDing function is performed by gate 69.

The output of the AND gate 74 is used to activate feedback to the operator when an EMG burst duration exceeds the on-time of monostable multivibrator 67. This AND gate, 74, is connected to provide an output only when EMG activity occurs during the end portion of a time slot. This end portion begins when the burst duration multivibrator 67 returns to its stable state. The output from AND gate 74 sets the stimulus control flip-flop 76. As long as flip-flop 76 remains set, electrical stimulation current from the gated stimulation source 70 flow through the operator.

In addition to setting the stimulus control flip-flop 76, the output of the excessive burst duration detection AND gate 74 triggers the monostable multivibrator 78 that is used to set the duration of the electrical stimulation pulse. At the end of the on-time of monostable multivibrator 78, the transition of its inverting output from logic level 0 to logic level 1 resets the stimulus control flip-flop 76. This ends the stimulation pulse. The combination of the R-S flip-flop 76 and the monostable multivibrator 78 is used rather than simply one monostable multivibrator. This is done to make the monostable multivibrator 78 available for timing the stimulus duration of both the right and the left stimulation channels.

An EMG burst having a duration in excess of the on-time of the burst duration monostable multivibrator 67 could result in multiple output pulses from AND gate 74. If these pulses were allowed to generate a volley of stimulation pulses, the accumulative effect of the stimulation pulses during a short time period could result in an unpleasant shocking effect. This situation is prevented by limiting the possible number of electrical stimulation pulses to one for each time slot. At the end of the maximum desired burst duration, the return of the multivibrator 67 to its stable state triggers the R-S flip-flop 79. The output of this flip-flop, 79, switches AND gate 75 so that it will pass information resulting from the detection of excessive EMG burst duration. After this information passes AND gate 75, it resets flip-flop 79, closing AND gate 75 to any further information flow until flip-flop 79 is set again at the appropriate time during the next time slot. Since the information used to prevent signal flow through gate 75 is obtained from its own output, the width of its output pulse is determined by the delay in the negative feedback path to its control input. OR gate 77 and multivibrator 78 are used in this negative feedback path to insure that the width of the output pulse of AND gate 75 is sufficient to set flip-flop 76 and trigger multivibrator 78.

The gated stimulation source 71 is used to inform the operator of the end of a time slot (T1 or T2 of FIG. 4). The transition from logic level 0 to logic level 1 which appears at the inverting output of the time slot duration monostable multivibrator 68 is used to trigger the stimulation duration monostable multivibrator 78 and the stimulation control R-S flip-flop 80. The stimulation control flip-flop 80 remains set for the on-time of the stimulation duration multivibrator 78, providing the gated stimulation source 71 with the required input to result in an electrical stimulation pulse of the desired duration.

Note from the tabulation of wheelchair control commands, FIG. 4, that EMG bursts are generated in both the right and the left EMG channel when and only when the wheelchair is to be stopped. The STOP command results in both flip-flop 72 and flip-flop 73 being set during time slot 1. As soon as this condition occurs, the STOP command is decoded by AND gate 83. This decoded output representing a STOP command passes through OR gate 84 and resets the four motor control flip-flops 85, 86, 87, and 88. The outputs from each of these flip-flops are amplified 89, 90, 91, and 92 so they can actuate relay solenoids 93, 94, 95, and 96 respectively. The RWF (right wheel forward) relay connects the drive motor battery 97 to the right wheel drive motor 98 with such a polarity as to turn the right wheel drive motor in a direction that would result in forward motion of the wheelchair. Corresponding functions are provided by the RWR (right wheel reverse) relay 94, the LWF (left wheel forward) relay 95, and the LWR (left wheel reverse) relay 96. With the resetting of all four motor control flip-flops 85, 86, 87, and 88 as a result of execution of the STOP command, all of the relays are deenergized, resulting in the stopping of any motor activity. In addition to stopping the wheelchair, the STOP command also results in the resetting of flip-flops 81, 82, and 100. The functions of these three flip-flops will become evident in the following explanation of the mechanism for decoding the RIGHT, LEFT, FORWARD, and REVERSE commands.

Memory of the occurrence of an EMG burst in the right channel during time slot 1 is retained by R-S flip-flop 81 after time slot 1 is over. This is accomplished by the setting of flip-flop 81 with the transition from logic level 0 to logic level 1 at the inverting output of flip-flop 72 that occurs at the end of time slot 1. Similarly, memory of a left channel EMG burst during time slot 1 is retained in R-S flip-flop 82 after time slot 1 is over.

Now consider the decoding of a RIGHT command. Note from the tabulation of wheelchair control commands, FIG. 4, that a right channel EMG burst is generated in both time slot 1 and time slot 2, with no activity on the left EMG channel. At the end of time slot 1, flip-flop 81 is left set in memory of the occurrence of the T1 interval right channel EMG activity. If during the second time slot the right EMG channel is again activated, flip-flop 72 becomes set again, resulting in a coincidence of both flip-flop 81 and flip-flop 72 being in the ON state. This coincidence results in an output from AND gate 103 which decodes a RIGHT command. The decoded output of AND gate 103 passes through OR gate 84 and resets any of the motor control flip-flops that may have previously been set. This negates any previous motor activation command. The output of AND gate 103 also sets flip-flop 87 after passing through OR gate 108 and being delayed for a few microseconds. The delay 111 prevents a race condition from occurring between the resetting and the setting of flip-flop 87. Such a race condition could result in uncertainty as to which state flip-flop 87 would be left in. The delay of a few microseconds would in no way be detected in the performance of the wheelchair because the mechanical time constants of the drive motor and loaded wheelchair exceed the few microseconds by many orders of magnitude. After execution of this command, the motor which drives the left wheel of the wheelchair will begin turning in such a direction as to drive the wheelchair forward. Since only the left wheel will be turning, the resultant motion of the wheelchair will be a right turn.

The technique of switching the right and left motors to achieve right turns, left turns, forward motion, and reverse motion is well known and has proven to be an effective way of manipulating a wheelchair. Known systems that are currently being used extensively perform this switching function with a set of switches that are mechanically coupled to a joy stick. These switches replace the relays 93, 94, 95, and 96.

The mechanism for decoding a left command is similar to that described above for the decoding of a right command, except that AND gate 104 detects the coincidence of left channel EMG activity in both time slots. This coincidence is detected when flip-flops 82 and 73 are in their ON states simultaneously, corresponding to flip-flops 81 and 72 being in their ON states simultaneously for the RIGHT command. The effect of the left command is to first stop any motor activity by resetting the motor control flip-flops 85, 86, 87, and 88. When after a few microseconds delay 109, the right wheel motor is energized with the polarity required to start the motor turning in a direction that would drive the wheelchair forward.

Note from the tabulation of wheelchair control commands, FIG. 4, that the forward command is made by making a right channel EMG burst during T1 and a left channel EMG burst during T2. Such EMG activity would result in a coincidence in the ON times of flip-flops 81 and 73. This coincidence is detected by AND gate 106. The output from the FORWARD decoding gate 106 causes any prior motor activity to be stopped and then both motors started in the appropriate direction to result in straight forward motion of the wheelchair. The REVERSE decoding gate 107 detects the required combination of a T1 left channel EMG burst and T2 right channel EMG burst. The output from the REVERSE decoder gate 107 causes any previous motor activity to be stopped and then both motors to start rotating in such a direction as to drive the wheelchair in a straight backwards motion.

Each of the wheelchair commands above initiates the appropriate reset activity to insure that a future command will not be misinterpreted due to residual memory in either flip-flop 81 or 82. All decoded command signals are ORed, 84, to reset these flip-flops (81 and 82). Since the STOP command is generally executed before the end of the first time slot and the other commands are generally executed before the end of the second time slot, provisions are made such that flip-flops 81 and 82 cannot be set by the return to stable state of flip-flops 72 and 73 respectively at the end of the first time slot for the STOP command and at the end of the second time slot for the other commands. These provisions are implemented by gating off the connection between flip-flop 72 and flip-flop 81 with AND gate 101 and also gating off the connection between flip-flop 73 and flip-flop 82 with AND gate 102 after the execution of the command. This is done by resetting the gate control flip-flop 100 with the decoded output from OR gate 84 which is common to all commands. When a new time slot is initiated by the operator for the purpose of issuing a new wheelchair control command, the output of monostable multivibrator 68 sets the gate control flip-flop 100 so the new EMG activity in the first time slot can be transferred to either flip-flop 81 or 82 for the purpose of being held in memory as is required for all commands except the STOP command.

The hard wired logic system of FIG. 5 is an example of one method of implementing the wheelchair digital control unit. An alternate approach would be to replace the portion of the system shown in FIG. 5 that is enclosed in dash lines with a programmed sequential processing device such as a microprocessor system. The two inputs (R EMG and L EMG) and the six outputs (LS, RS, RWF, RWR, LWF, and LWR) could all be TTL or CMOS compatible.

Figure 6:
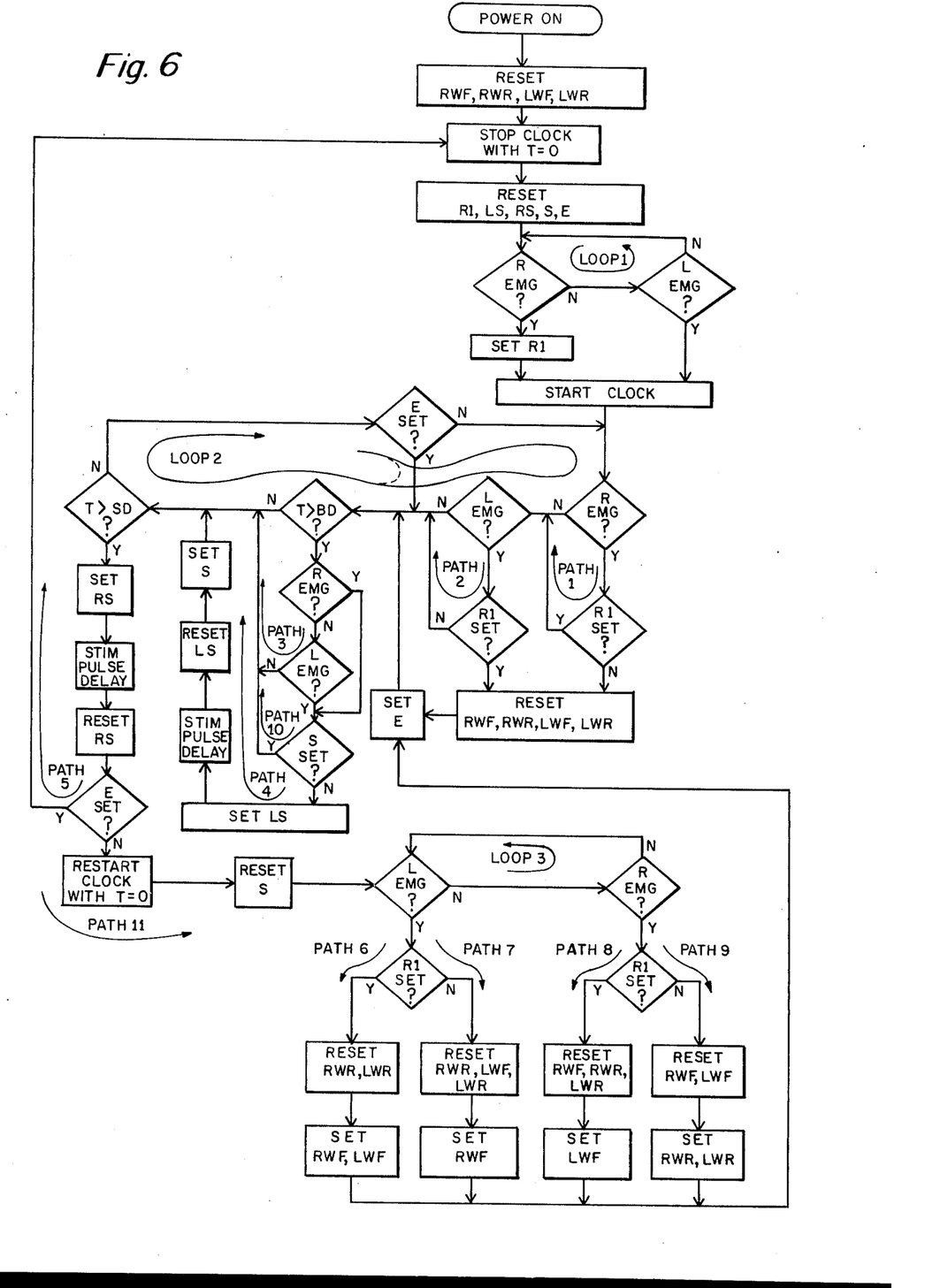
FIG. 6 is a representative flow chart for a microprocessor that could be used as the digital control unit shown in FIG. 2.

A typical sequence of events for the information processing of an appropriate microprocessor system is shown in the flow-chart of FIG. 6. The specific program to result in execution of this sequence of events would be dependent upon the specific instruction set for the particular microprocessor used. Straight forward programming techniques can be used to derive the program from the flowchart. The resultant program is stored in ROM (read only memory) so program execution begins as shown in FIG. 6 as soon as power is applied.

The first operation after power is applied is to set the four one-bit output ports that control the drive motors to logic 0 (Reset RWF, RWR, LWF, and LWR). This operation insures that the wheelchair will remain stationary until commanded to go by the operator.

Next, a clock used to time the sequential time slots (T1 and T2 of FIG. 4) and the durations of EMG bursts is reset to a known state, corresponding to T (time) equal to zero, and it is left stopped in that state. Five one-bit flags that serve as a scratchpad memory (R1, LS, RS, S, and E) are then initialized to the state (all logic 0's) that indicates that the microprocessor is not in the process of serving an operator's command.

At this point in the operation, system initialization has been completed and Loop 1 is entered. While in this loop, both the right channel and the left channel EMG input ports are continuously polled to detect any signal from the operator. The appearance of a logic 1 at either input port will result in an exit from Loop 1. If the exit results from EMG activity in the right channel, flag R1 is set (to logic 1) providing memory of a right channel signal during the first time slot. Upon acknowledging a signal from either channel, the clock is started to allow timing of EMG burst and time slot durations.

After starting the clock, Loop 2 is entered. Both EMG channels are polled in this loop. Also, the time is checked for the expiration of the EMG burst duration BD. (BD is the maximum burst duration that the operator can generate without receiving notification of excessive muscular activity.) Another function performed in Loop 2 is the continual checking for expiration of the predetermined time slot duration (SD) for the time interval T1 of FIG. 4. The result of the E set check in Loop 2 is negative during this stage of the information processing because the E flag is only set at a later stage in the operation. Since the E flag is not set, the truncated alternate of Loop 2 (indicated by dashed lines) is not yet in effect.

During the initial period of traversing Loop 2, the EMG input port that was activated to result in entry of the loop remains at logic 1. The state of this EMG input port may fluctuate between logic 1 and logic 0 for the duration of the EMG burst. When a poll indicates logic 1, the result is a minor excursion (either Path 1 or Path 2) from Loop 2. If Loop 2 had been entered by activation of the right channel, the right EMG check would be positive at times during this initial period, resulting in a minor excursion via Path 1 to check the R1 flag. Upon finding this flag set, control would be returned to the main Loop 2. There is also shown in FIG. 6 a corresponding excursion (Path 2) that would result during the EMG burst if Loop 2 had been initially entered by a signal on the left EMG channel. A return to the main loop from this excursion would result from the negative result of the R1 flag check.

The purpose of the two excursions described above (Path 1 and Path 2) is to provide for exit from Loop 2 for the execution of a STOP command. To stop the wheelchair, the operator signals both EMG channels during the T1 time slot. If the right EMG had been first acknowledged while in Loop 1, the left EMG would be detected at some time during the T1 time slot while in Loop 2. The R1 flag check in Path 2 following the positive result of the left EMG check would also be positive, resulting in an exit from Path 2 and the resetting of RWF, RWR, LWF, and LWR. This would stop the wheelchair. Similarly, if the left EMG channel had been acknowledged first while in Loop 1, the appearance of a right channel EMG while in Loop 2 would result in an excursion into Path 1. While in Path 1, the R1 flag would be found not to be set (because of entry into Loop 2 from a left channel EMG signal). This would cause exit from Path 1 to reset RWF, RWR, LWF, and LWR which would stop the wheelchair.

After the wheelchair is stopped as described above, the E flag is set before reentry into Loop 2. (This flag is set to allow resetting the system for a new command at the end of the T1 time slot.) After Loop 2 is reentered, the flow of microprocessor instruction execution sequences around the truncated alternate to Loop 2 that is indicated by dashed lines. Provision for truncating Loop 2 after the STOP command is not necessary because continual excursions through the reset RWF, RWR, LWF, and LWR operation would make no difference in system performance. However, the E flag is also used with other commands (described below) where truncating Loop 2 is essential to prevent a spurious STOP.

The next event in the sequence of information processing while servicing a STOP command is the exit from Loop 2 resulting from a positive result of the T>BD check. Immediately following this exit from Loop 2, both EMG inputs are polled. If no EMG activity is detected, indicating that the EMG burst duration does not exceed BD, control is returned to Loop 2 via Path 3. If there is EMG activity on either channel, indicating that the burst duration has exceeded BD, a check is made to determine if feedback has already been given to the operator regarding the excessive burst duration. This check is done by testing the S flag. If the S flag is set, indicating prior notification to the operator of his excessive burst duration, repetitive notification is avoided and control is returned to Loop 2 via Path 10.

If the S flag is not set, indicating no prior notification to the operator of his excessive burst duration, left stimulus channel output LS is set. This gates on electrical stimulation current to the operator. Further operation is then delayed for the predetermined stimulus pulse duration period. At the end of this period, the LS output port is reset terminating the electrical stimulation pulse. Before returning to Loop 2, the S flag is set to prevent repetitive stimulation from occurring during future passes around Loop 2 throughout the remainder of the T1 time slot. The next exit from Loop 2, other than excursions via Path 3 or Path 10, occurs when the time exceeds time slot duration SD.

After exit from Loop 2 at the end of the T1 time slot, the operator is notified that the time slot is over. The system executes this notification by setting the RS output port which results in the gating on of stimulus current, the delaying for the predetermined stimulus pulse duration, and the resetting of the RS output port.

After notifying the operator of the end of a time slot, a check is made to determine if that time slot was the last time slot of a command. (Note that T1 is the only and last time slot of the STOP command and T2 is the last time slot of the other commands.) This check is made by testing the E flag which is set upon the execution of any command. For the condition currently being discussed, specifically where a STOP command had been executed, the result of the E flag test would be positive. This would cause an exit via Path 5 to the system initiation procedure that would put the system on standby for the processing of a new command.

Now consider the processing of commands other than the STOP command. As shown in the wheelchair command table of FIG. 4, the STOP command is the only command having an EMG burst in both channels during time slot 1. For the other commands there would be no exit from either Path 1 or Path 2 to reset the motor control outputs during time slot 1 because EMG activity would be present on only one input channel during time slot 1. Since neither of these exits would take place, the E flag would not be set during time slot 1. As a result, the exit via Path 5 discussed above would not occur after time slot 1. Instead, Path 11 would be taken. This would result in resetting the clock for T=0 and starting the clock again so the second time slot (T2) can be timed. After restarting the clock, the S flag is reset. This will insure that the operator will receive the appropriate feedback should his burst duration in the second time slot exceed BD.

The next stage in the information processing is to remain in Loop 3 waiting for an EMG burst in the second time slot. As soon as the T2 EMG burst arrives, the microprocessor has the required information to decode the command since the state of the R1 flag constitutes memory of which EMG channel was activated during the T1 time slot. As can be verified from the wheelchair command table FIG. 4, a FORWARD command will result in Path 6, a LEFT command will result in Path 7, a RIGHT command will result in Path 8, and a REVERSE command will result in Path 9. For each of these four paths, the motor control functions that should not be activated for the appropriate command are reset because they could have been set for the previous command. Following these resettings, the motor control outputs are set as required to execute the decoded command.

Upon completion of any command, the E flag is set and control is returned to the truncated version of Loop 2. This provides for notification to the operator of a T2 EMG burst exceeding BD and for notification of the end of the T2 time slot. Following the latter notification, Path 5 is taken to reinitialize the system to await a new wheelchair control command.

The wheelchair control system described above is just one example of an application for the direct-electrical man-machine interface system. The passage of messages with alphanumeric characters (conventional letters, numbers and punctuation marks) over the direct-electrical man-machine interface is another application. Only one channel would be required for Morse code if a dash were coded as two pulses close together in time and a dot were coded as one pulse. The morse code could be passed faster with two channels, one for dots and the other for dashes. A still faster method would be to pass all the information required for one alphanumeric character during the time required for one pulse by using more channels, for example, five or eight channels with codes such as the standard 5-level binary permutation code or the 8-level ASCII teletypewriter code.

The afferent (information flow to the operator) portion of a direct-electrical interface system using a teletype code would consist of typically five or eight channels each typically consisting of the components of FIG. 2 that are numbered as 41, 42, 43, 44, 45, 46. Each output bit of the five or eight bit word from a computer, microprocessor, or teletype terminal would be routed to one of the interface channels. The five or eight bit words could be sent from the computer at a predetermined rate, or an EMG channel could be used for strobing the successive words from the computer at a rate determined by the operator. A simple method of implementing the strobing function would be to use a standard EMG pulse of the type derived from the triggered monostable multivibrator 38 of FIG. 2 as a substitute for the ready flag of conventional computer terminals. The rate at which the computer puts out alphanumeric characters would be slowed to the rate at which the operator could comprehend them, rather than to the rate at which the mechanical processes of a teletype terminal could decode and print them.

Figure 7:
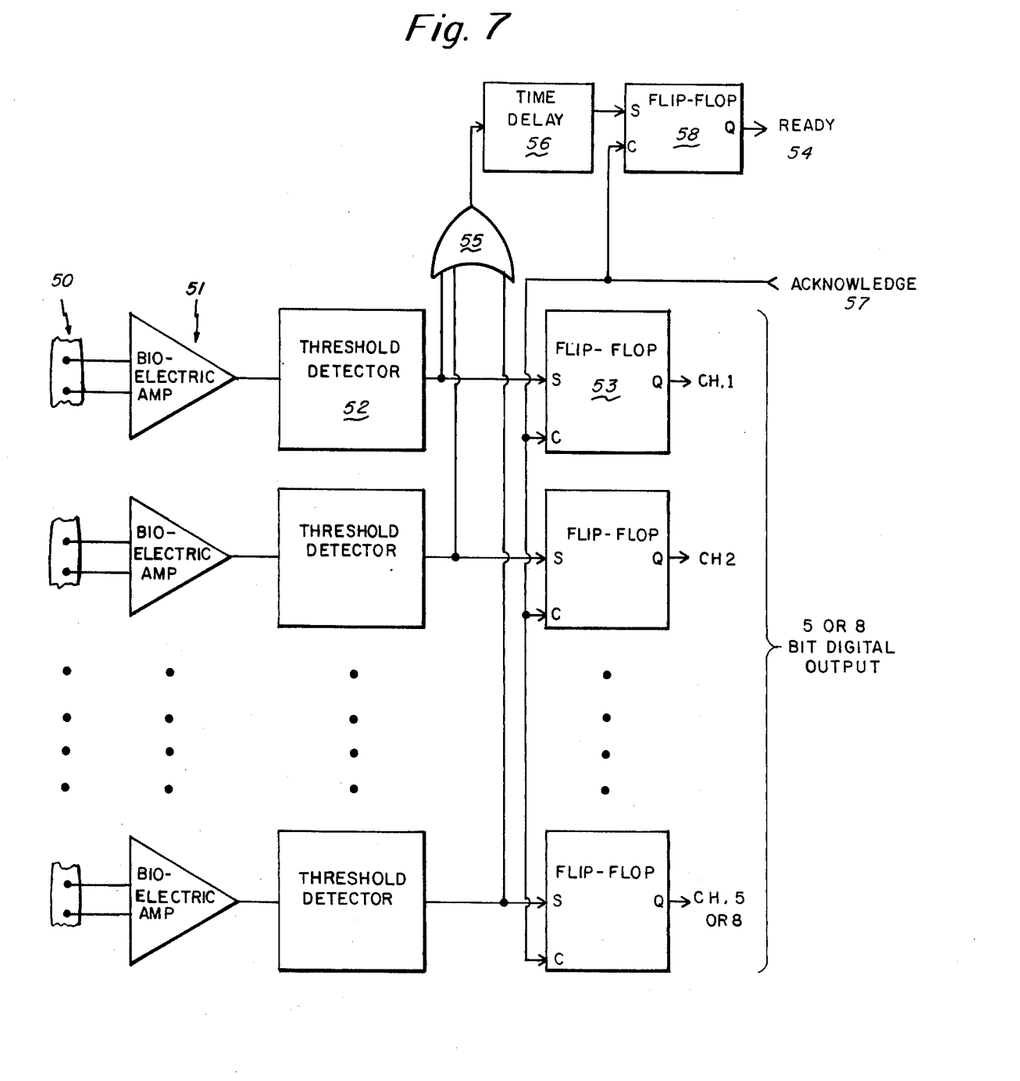
FIG. 7 is a simplified block diagram for the efferent portion of a direct-electrical interface system using a teletype code.

A simplified block diagram for the efferent (information flow from the operator) portion of a direct-electrical interface system using a teletype code is shown in FIG. 7. Each channel has electrodes 50, provisions for bioelectric amplification 51, and a threshhold detector 52, all of which serve analogous functions to the corresponding components of both FIG. 1 and FIG. 2. The output of each threshhold detector sets a set-clear flip-flop when an amplified bioelectric burst for the given channels exceeds the threshhold. As a result of this action, the set of five (or eight) flip-flops act as a buffer register that holds the binary coded alphanumeric character that originated from electrical activity in the body of the operator.

Since all the required bioelectric bursts for an alphanumeric character will not be generated at precisely the same time, the computer must wait for all of them to arrive before decoding. The wait period is provided by time delay 56. It is set for the maximum expected delay between the first and last bioelectric bursts of a set that the operator attempts to generate simultaneously for one alphanumeric character. The first burst passes through OR gate 55 to initiate the time delay 56. The time delay 56 is implemented with a non-retriggerable monostable multivibrator so that the remaining bursts of the set do not cause the delay period to stretch out. The transition of the monostable multivibrator to its stable state is used to set flip-flop 58. The output of this flip-flop provides a ready signal 54 that instructs the computer to read in the alphanumeric character. After receiving the alphanumeric character, the computer sends out an acknowledge pulse 57 that resets all the flip-flops in the system of FIG. 7, leaving it ready to pass another alphanumeric character.

What is claimed is:

1. Apparatus for providing direct electrical transfer of information between a subject and a digital system comprising;
    a plurality of individually isolated myo-electric responsive electrode means each for detecting an independently distinguishable myo-electric activity signal generated by the subject,
    means for supporting the electrode means each at a selected site on the subject with adjacent electrode means being sufficiently spaced to permit interpretation of each of the independent myo-electric activity signals,
    means for amplifying each of said myo-electric signals,
    and means, during a predetermined time period, for separately and directly converting each amplified myo-electric signal into a representative binary signal the state of which is dependent upon the absence or presence of said myo-electric signal, said binary signals collectively forming a binary word code, a plurality of lines corresponding on a one-to-one basis with and coupling from the converting means and forming a digital information bus, and means coupling to the digital information bus for decoding the binary word code to provide a signal representative of the particular code presented on the digital information bus.

2. Apparatus as set forth in claim 1 wherein said means for converting includes threshold detection means for each signal responsive to the signal attaining said threshold and means responsive to the output from said threshold detection means for registering a signal indicative of one binary state.

3. Apparatus as set forth in claim 2 wherein said binary state for a signal registered by attaining said threshold is a binary "one".

4. Apparatus as set forth in claim 2 wherein said means for registering includes a bistable means one being associated with each threshold detectable signal and all connected directly to separate lines of said digital information bus.

5. Apparatus as set forth in claim 4 wherein said bistable means includes a flip-flop, and means for periodically clearing all flip-flops.

6. Apparatus as set forth in claim 1 further comprising digital processing means for receiving the digital signal.

7. Apparatus as set forth in claim 1 comprising stimulation means for providing a stimulation pulse to the body.

8. Apparatus as set forth in claim 1 for controlling drive means for a wheelchair to generate left, right, forward, reverse and stop commands to the drive means.

9. Apparatus as set forth in claim 1 including stimulation means for providing a stimulation pulse to the body and means for controlling the stimulation means upon receipt of a bioelectric activity signal.

10. Apparatus as set forth in claim 9 wherein the stimulation means is operated only when the bioelectric activity signal persists for greater than a preselected period.

11. Apparatus as set forth in claim 9 including means for adjusting the duration of the stimulation pulse.

12. Apparatus as set forth in claim 9 including two stimulation means coupling to the same area of the body where the two electrode means are disposed and separate control means for each stimulation means, one control means being responsive to bioelectric activity signals of predetermined duration while the other control means is responsive to the end of a time slot.

13. Apparatus for providing direct electrical transfer of information between a digital system and a subject comprising:

a plurality of stimulating electrode means each for applying independently distinguishable electrical stimulation to the subject, means including encoding means, operable during a predetermined time period, for establishing a plurality of separate binary signals, said binary signals collectively forming a binary word code, a plurality of lines corresponding on a one-to-one basis with and coupling from the means for establishing and forming a digital information bus having the binary word code expressed thereon, means coupling the plurality of lines as a digital information bus directly to the plurality of electrode means on a one-to-one basis whereby stimulation signals are selectively applied to the electrode means to collectively generate a coded stimulation pattern interpretable by the subject.

14. Apparatus as set forth in claim 13 wherein said means coupling includes pulse generating means.

15. Apparatus as set forth in claim 13 wherein each said electrode means is for detecting one of a set of independent bioelectric activity signals, and further comprising amplifying means and means for converting each detected signal into a bit of information coupled to said digital information bus.

16. A method of providing direct electrical transfer of information from a digital system to a subject, comprising the steps of, providing a plurality of stimulating electrode means each for applying independently distinguishable electrical stimulation to the subject, during a predetermined time period establishing a plurality of separate binary signals, said binary signals collectively forming a binary word code only present during the predetermined period, providing a plurality of lines for coupling the binary signals on a one-to-one basis, said lines forming a digital information bus having the binary word code expressed thereon, converting the binary signal on each line to one of the absence and presence of a stimulation signal and applying the stimulation signal when present, to the associated electrode means whereby the subject receives a bioelectric activity signal which is a collectively generated coded stimulation pattern interpretable by the subject.

17. A method as set forth in claim 16 wherein "ones" of the byte are converted as a stimulation pulse while "zeros" represent the absence of a stimulation pulse.

18. A method of providing electrical transfer of information from a subject to a digital system, comprising the steps of, providing a plurality of individually isolated myo-electric responsive electrode means, each said electrode means for detecting one of a set of independently distinguishable myo-electric activity signals, amplifying each of the detected myo-electric signals, and during a predetermined time period, separately and directly converting each amplified myo-electric signal to a representative binary signal the state of which is dependent upon the absence or presence of said myo-electric signal, said binary signals collectively forming a binary word code, providing a plurality of lines for coupling the binary signals on a one-to-one basis, said lines forming a digital information bus having the binary word code expressed thereon and decoding the binary word code to provide a signal representative of the particular code presented on the digital information bus.

19. A method as set forth in claim 18 including feeding back to the subject a signal when the subject develops a bioelectric signal amplitude or duration that exceeds a threshold.

* * * * *